United States Patent
Baudin et al.

(10) Patent No.: US 6,544,964 B1
(45) Date of Patent: Apr. 8, 2003

(54) METHOD FOR FIXING OR SEPARATING IONS, IN PARTICULAR OF LEAD, USING PER(3,6-ANHYDRO)CY-CLODEXTRIN DERIVATIVES

(75) Inventors: Cécile Baudin, Paris (FR); Bruno Perly, La Verrière (FR); Andrée Gadelle, Montbonnot (FR); Jean-Claude Debouzy, La Tronche Cedex (FR); Florence Fauvelle, Grenoble (FR)

(73) Assignee: Commissariat A L'Energie Atomique, Paris (FR)

( * ) Notice: Subject to any disclaimer, the term of this patent is extended or adjusted under 35 U.S.C. 154(b) by 0 days.

(21) Appl. No.: 09/445,818
(22) PCT Filed: Jun. 12, 1998
(86) PCT No.: PCT/FR98/01235
§ 371 (c)(1),
(2), (4) Date: Mar. 24, 2000
(87) PCT Pub. No.: WO98/56829
PCT Pub. Date: Dec. 17, 1998

(30) Foreign Application Priority Data

Jun. 13, 1997 (FR) .............................. 97 07339

(51) Int. Cl.[7] ...................... A61K 31/715; A61K 33/24; C08B 37/16
(52) U.S. Cl. .................... 514/58; 424/652; 536/103
(58) Field of Search ............. 536/103; 514/58; 424/652

(56) References Cited

U.S. PATENT DOCUMENTS 5,567,499 A   10/1996   Cundiff et al.
5,792,857 A * 8/1998    Baudin et al. .............. 536/103

FOREIGN PATENT DOCUMENTS

EP  0722826  7/1996
FR  2740383  4/1997

OTHER PUBLICATIONS

Ashton, P. et al "A novel approach to the synthesis of some chemically–modified cyclodextrins" J. Org. Chem. vol. 60, pp. 3898–3903, 1995.*
H. Yamamura et al., "A Cyclodextrin Derivative with Caution Carrying Ability: Heptakis (3,6–anhydro)–β–cyclodextrin 2–O–p–Phenylazobenzoate," Chemistry Letters, vol. 9, JP, (1996); 799–800.
F. Fauville et al., "Letter: Electrospray ionisation and matrix–assisted laser desorption/ionisation mass spectrometric studies of cation complexation with per–3, 6–anhydro–α–cyclodextrin," European Mass Spectrometry, vol. 2, No. 6, (1996): 381–384.
Gadelle A, et al., (1991), "Selective Halogenation at Primary Positions of Cyclomaltooligosaccharides and a Synthesis of Per–3,6–anhydro Cyclomaltooligosaccharide", Chem. Int. Ed. Engl., 30:78–79.
Ashton, P.R. et al., (1991), "Synthesis and Characterization of Per–3,6–anhydro Cyclodextrins", Chem., Int. Ed. Engl., 30:80–81.
Yamamura H., et al., (1991), "Preparation of Heptakis (6–O–(p–tosyl))–β–cyclodextrin and Heptakis (6–O–(p–tosyl))–2–O–(p–tosyl)–β–cyclodextrin and Their Conversion to Heptakis(3,6–anhydro)–β–cyclodextrin", Chem. Pharm. Bull., 39:2505–2508.
Yamamura H., et al., (1993), "Preparation of Octakis(3, 6–anhydro)–γ–cyclodextrin and Characterization of its Cation Binding Ability", J. Chem. Soc., Chem. Commun., pp. 636–637.
Yamamura H., et al., (1995), "Synthesis and Alkali Metal Ion Binding of Poly(3,6–anhydro)–α–cyclodextrins", Tetrahedron Letters, 36(7):1093–1094.

* cited by examiner

Primary Examiner—James O. Wilson
Assistant Examiner—Leigh C. Maier
(74) Attorney, Agent, or Firm—Burns, Doane, Swecker & Mathis LLP

(57) ABSTRACT

The invention relates to the fixation or separation of ions, particularly of Pb, by per(3,6-anhydro)cylcodextrin derivatives.

This can be carried out by contacting the medium containing the ions to be fixed or separated, with a per(3, 6-anhydro)cylcodextrin derivative of formula:

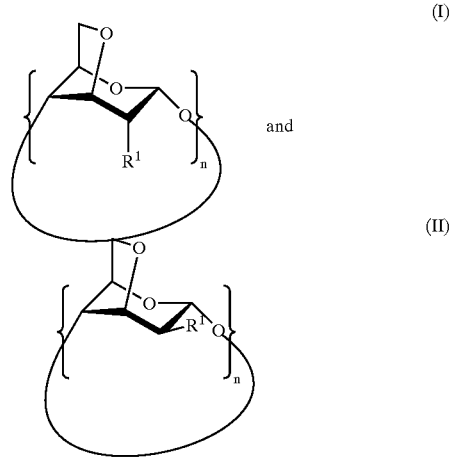

in which at least one of the $R^1$ represents $OCH_3$, whilst the other $R^1$ can represent $OCH_3$, OH or other groups, for complexing the ions.

Preferably, for the fixation of lead, the derivative complies with formula (I) with n=6 and all the $R^1=OCH_3$.

11 Claims, 1 Drawing Sheet

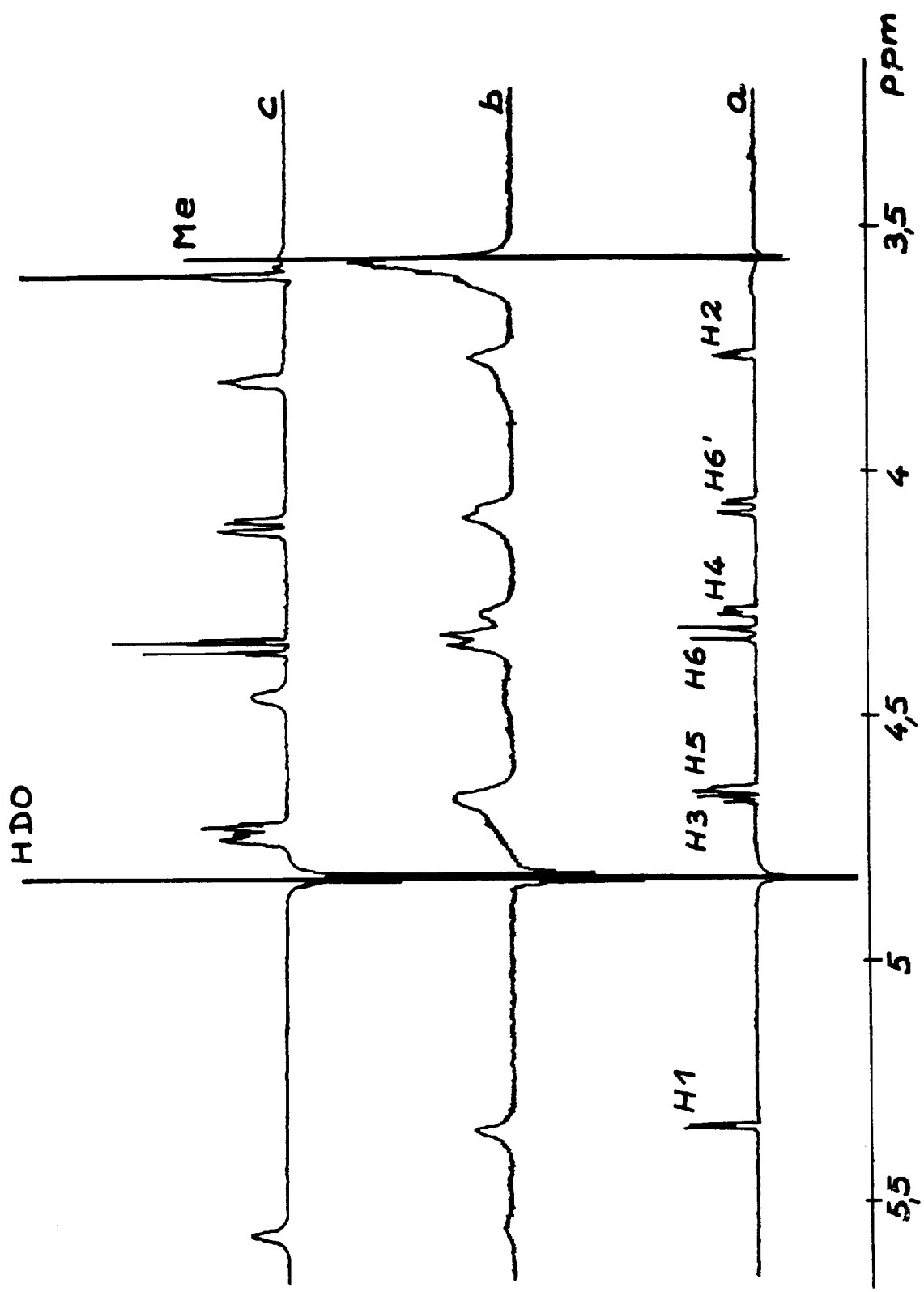

METHOD FOR FIXING OR SEPARATING IONS, IN PARTICULAR OF LEAD, USING PER(3,6-ANHYDRO)CY-CLODEXTRIN DERIVATIVES

TECHNICAL FIELD

The present invention relates to a process for the fixation or separation of ions, particularly of Pb, by per(3,6-anhydro) cylcodextrin derivatives.

PRIOR ART

Cyclodextrins or cyclomaltooligosaccharides are compounds having a natural origin formed by the linking of glucose units which are α(1,4)-bonded.

Numerous works have revealed that these compounds could form inclusion complexes with hydrophobic molecules, thus permitting their solubilization in aqueous media. Numerous applications have been proposed for taking advantage of this phenomenon, particularly in the pharmaceutical field, as is described by D. Duchêne "Pharmaceutical application of cyclodextrins" in "Cyclodextrins and their industrial uses", D. Duchêne, Editions de Santé, Paris, 1987, pp 213–257.

Pharmaceuticals have already been marketed in Japan, Italy and more recently in France, in the form of complexes in cyclodextrins. In France, the first active principle marketed in the form of an inclusion complex in a cyclodextrin is piroxicam, which is an anti-inflammatory agent marketed by Pierre Fabre Medicament under the name BREXIN[(R)]. Among the very numerous modified derivatives of said cyclodextrins, those for which the cavity is turned on itself have interesting properties, even though their capacity to include organic molecules is lost or very limited. Compounds of this type are per(3,6-anhydro)cyclodextrins.

The synthesis of said peranhydrocyclodextrins has been described as from 1991 in document 1: Gadelle A. and Defaye J., Angew. Chem. Int. Ed. Engl., 1991, 30, 78–79; and document 2: Ashton P. R., Ellwood P., Staton I. and Stoddart J. F., Angew. Chem. Int. Ed. Engl., 1991, 30, 80–81) and it has been demonstrated that these derivatives have interesting solubilities both in water and organic solvents. Several subsequent studies (document 3: Yamamura H. and Fujita K. Chem. Pharm. Bull., 1991, 39, 2505–2508; document 4: Yamamura H., Ezuka T., Kawase Y., Kawai M., Butsugan Y. and Fujita K., J. Chem. Soc., Chem. Com., 1993, 636–637; and document 5: Yamamura H., Nagaoka H., Kawai M. and Butsugan Y., Tetrahedron Lett. 1995, 36, 1093–1094) have also demonstrated that these peranhydro derivatives could complex alkaline ions with a non-negligible selectivity.

Ashton et al in J. Org. Chem., 60, 1995, pp 3898–3903, have described the synthesis of the pernanhydro-β-cyclodextrin derivative substituted in the 2-position by a methyl group.

However, this chemical modification has not been carried out with a view to optimizing the complexing or selectivity properties of the peranhydrocyclodextrins.

DESCRIPTION OF THE INVENTION

The present invention relates to the use for the separation or fixation of ions of derivatives of peranhydrocyclodextrins in which a chemical modification has been carried out for modifying their properties, particularly their selectivity with respect to the ions which they are liable to complex and in particular with respect to lead.

According to the invention, this modification relates to the hydroxyl groups present on said molecule, as well as the configuration of carbon $C_2$, which can be reversed for leading to L-mannose-type derivatives.

Thus, the invention relates to a process for the fixation or separation ions, which consists of contacting a medium containing said ions with a derivative of per(3,6-anhydro) cyclodextrin, complying with one of the following formulas:

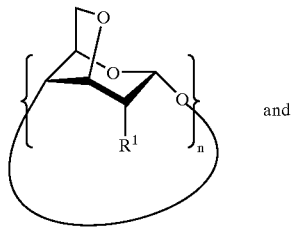

(I)

and

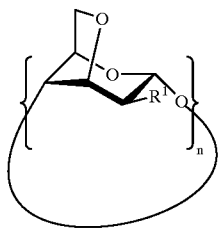

(II)

in which at least one of the $R^1$ represents the methoxy group and the other $R^1$, which can be the same or different, represent a group complying with one of the formulas: OH, $OR^2$, SH, $SR^2$, $OCOR^2$, $NH_2$, $NR^2R^3$, $CONR^2R^3$, $CONH_2$, CN, $COOR^2$, COOH and $R^2$, in which $R^2$ represents a saturated or unsaturated, aliphatic or aromatic, hydrocarbon group, which can have one or more heteroatoms chosen from among O, S and N, and $R^3$ represents a hydrogen atom or a saturated or unsaturated, aromatic or aliphatic, hydrocarbon group, which can have one or more heteroatoms chosen from among O, S and N, and n is equal to 6, 7 or 8, for fixing said ions in complex form with the per(3,6-anhydro)cyclodextrin derivative and for separating them from said medium.

In the cyclodextrin derivative of formula (I) or (II), the aliphatic or aromatic, hydrocarbon groups which can be used for $R^2$ and $R^3$ can be of various types. They are constituted by a carbon chain, in which certain carbon atoms can be replaced by one or more heteroatoms such as O, S and N and can have one or more ethylene or acetylene unsaturations. Moreover, the hydrocarbon group can have different substituents, in particular functional groups or halogen atoms. The aromatic hydrocarbon groups can be constituted by the optionally substituted tosyl group and phenyl group, e.g. by alkyl groups having 1 to 20 carbon atoms. $R^2$ and $R^3$ can in particular represent a straight or branched, alkyl group having 1 to 20 carbon atoms.

According to a preferred embodiment of the invention, intended more particularly for the separation of lead ions, the per(3,6-anhydro)cyclodextrin derivative is an β-cyclodextrin derivative, i.e. in the aforementioned formulas (I) and (II), n is equal to 6.

Preferably, the derivative used complies with formula (I), in which all the $R^1$ represent the methoxy group and n is equal to 6.

The ions which can be fixed or separated by the process according to the invention can be of various types. They can e.g. be ions of alkali metals, actinides, lanthanides or polluting metals such as lead, mercury, cobalt and strontium.

The process according to the invention more particularly applies to the separation and fixation of lead in complex form.

Thus, lead and its derivatives pollute the environment and are toxic both to man and animal. The main toxic effects affect the neurological development and the functioning of the nervous system. It is consequently necessary to separate and eliminate lead from the environment and store it safely.

In addition, products which would make it possible to ensure the lead decontamination of living beings by preventing the action of lead on the nervous system and on other organs, would be of great interest for solving these problems.

According to the invention, it has been found that derivatives of per(3,6-anhydro)cyclodextrins complying with the above formulas (I) and (II), have a high specificity for lead and are capable of complexing it with high yields able to reach 100%, even in the presence of other ions, such as sodium ions.

Thus, it is possible to separate the lead from the surrounding medium in complex form.

The invention also relates to complexes of lead and derivatives of per(3,6-anhydro)cyclodextrins of formulas (I) or (II) described hereinbefore.

For implementing the process according to the invention, it is possible to use the per(3,6-anhydro)cyclodextrin derivative of formula (I) or (II) in the form of an aqueous solution or organic solution.

When the medium containing the ions to be separated or fixed is an aqueous solution, it is possible to dissolve the cyclodextrin derivative in an organic solvent which is immiscible with the aqueous solution, e.g. in chloroform, in order to form the complex in the organic solution and separate it easily from the aqueous solution.

It is also possible to use the cyclodextrin derivative in aqueous solution, particularly for the lead decontamination of living beings.

Thus, it is known that cyclodextrin derivatives of formulas (I) or (II) are biocompatible compounds. They can consequently be administered to man or animals for ensuring the fixation of the lead in complex form and thus prevent its interaction with the organs of the human or animal body.

The invention also relates to a pharmaceutical composition for the lead decontamination of a living being, characterized in that it comprises a per(3,6-anhydro)cyclodextrin derivative complying with one of the following formulas:

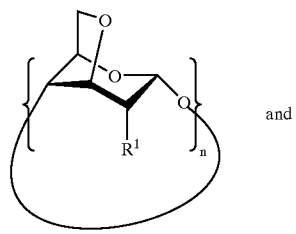

(I)

and

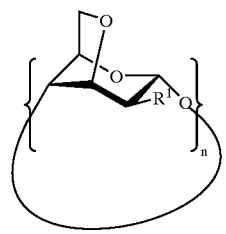

(II)

in which at least one of the $R^1$ represents the methoxy group and the other $R^1$, which can be the same or different, represent a group complying with one of the formulas: OH, $OR^2$, SH, $SR^2$, $OCOR^2$, $NH_2$, $NR^2R^3$, $CONR^2R^3$, $CONH_2$, CN, $COOR^2$, COOH and $R^2$, in which $R^2$ represents a saturated or unsaturated, aliphatic or aromatic, hydrocarbon group, which can have one or more heteroatoms chosen from among O, S and N, and $R^3$ represents a hydrogen atom or a saturated or unsaturated, aliphatic or aromatic, hydrocarbon group, which can have one or more heteroatoms chosen from among O, S and N, and n is equal to 6, 7 or 8.

Preferably, the per(3,6-anhydro)cyclodextrin derivative used in this composition complies with formula (I), in which all the $R^1$ represent the methoxy group and n is equal to 6.

This composition can be administered orally or by injection.

The aqueous solutions can incorporate up to 0.08 mole/l of the derivative of formula (I).

The administered quantities will depend on the lead contamination level and the weight of the patient.

The invention also relates to per(3,6-anhydro) cyclodextrin derivatives, usable in this process and which comply with one of the following formulas:

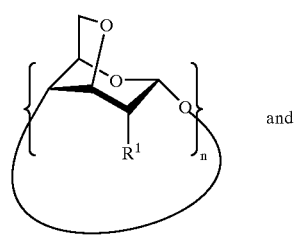

(I)

and

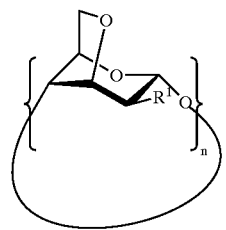

(II)

in which at least one of the $R^1$ represents the methoxy group and the other $R^1$, which can be the same or different, represent a hydrogen atom or a group complying with one of the formulas: OH, $OR^2$, SH, $SR^2$, $OCOR^2$, $NH_2$, $NR^2R^3$, $CONR^2R^3$, $CONH_2$, CN, $COOR^2$, COOH and $R^2$, in which $R^2$ represents a saturated or unsaturated, aliphatic or aromatic, hydrocarbon group, which can have one or more heteroatoms chosen from among O, S and N, and $R^3$ represents a hydrogen atom or a saturated or unsaturated, aliphatic or aromatic, hydrocarbon group, which can have one or more heteroatoms chosen from among O, S and N, and n is equal to 6, 7 or 8, provided that all the $R^1$ do not represent $OCH_3$ when n=7 and that the derivative complies with formula (I).

The cyclodextrin derivatives used in the invention can be prepared by different processes.

When the cyclodextrin derivative complies with the above formula (I) or (II), in which at least one of the $R^1$ represents the methoxy group, the other $R^1$ representing OH or $OCH_3$ and n is equal to 6, 7 or 8, they can be prepared by a process having the following stages:

1) reacting a peranhydrocyclodextrin complying with one of the formulas:

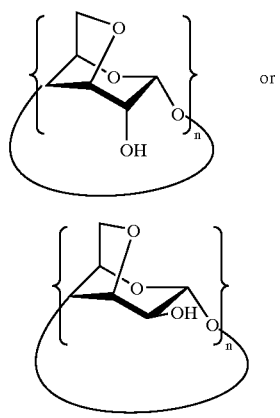

in which n is equal to 6, 7 or 8, with an alkali metal hydride for converting the OH group or groups into OM group or groups with M representing an alkali metal, 2) reacting the modified peranhydrocyclodextrin obtained in 1), with a methyl halide of formula $CH_3X$, in which X represents a halogen atom and 3) if necessary, reacting the peranhydrocyclodextrin obtained in 2) with one or more reagents in order to substitute it by $R^1$ groups differing from $OCH_3$.

For performing stage 2), use is made of the quantity of $CH_3X$ necessary for modifying one or more of the OH groups of the cyclodextrin.

When the cyclodextrin derivative complies with the above formulas (I) or (II), in which the other R1 represent $OR^2$, with $R^2$ having the meaning given hereinbefore, except $CH_3$, the above procedure is adopted for introducing the $OCH_3$ group or groups, followed by reacting the derivative with a halide of formula $R_2X$, in which $R^2$ has the meaning given hereinbefore and X is a halogen atom.

When the cyclodextrin derivative complies with formula (I) or (II), in which the other $R^1$ represent $OCOR^2$, the above procedure is adopted for first introducing the methoxy groups and then the methyl derivative is reacted with an acid anhydride or halide of formulas $R_2COX$ or $(R^2CO)_2O$, in which $R^2$ has the meaning given hereinbefore and X represents a halogen atom, in order to replace the remaining hydroxyls by $OCOR^2$.

When it is wished to prepare a cyclodextrin derivative, in which the other $R^1$ represent a halogen atom or a group of formula SH, $SR^2$, $NH_2$, $NR^{2R3}$, $CONR^2R^3$, $CONH_2$, CN, $COOR^2$, COOH, or $R^2$, with $R^2$ and $R^3$ having the meanings given hereinbefore, and n is equal to 6, 7 or 8, it is possible to carry out the following stages starting with a partly methylated peranhydrocyclodextrin, i.e. in which at least one of the $R^1$ represents $OCH_3$ and the other $R^1$ represent OH and performing the following stages:

1) reacting said peranhydrocyclodextrin with an alkali metal hydride for converting the OH group or groups into OM group or groups with M representing an alkali metal, 2) reacting the modified peranhydrocyclodextrin obtained in 1) with a chloride of formula $ClSO_2R^2$ with $R^2$ having the meaning given hereinbefore, for obtaining the derivative of formula (I) or (II), in which at least one of the $R^1$ is a group of formula $OSO_2R^2$ and 3) reacting the derivative obtained in the second stage with one or more appropriate reagents for replacing $OSO_2R^2$ by the desired $R^1$ group.

In this process, the per(3,6-anhydro)cyclodextrin is firstly transformed into alkoxide by the action of alkali metal hydride and said alkoxide is then converted into a derivative having a starting group of formula $OSO_2R^2$, which is then reacted in one or more stages with one or more appropriate reagents for replacing said starting group by the desired $R^1$ group.

Thus, in the case where $R^1$ has to represent $NH_2$, it is possible to react $N_3M$ and the compound defined in 2). The thus obtained compound, called an azide, can undergo a catalytic hydrogenation or can be treated in the presence of ammonia $NH_3$, in order to obtain the product where $R^1$ is to represent $NH_2$.

The product where $R^1$ is to represent $NR^2R^3$ is obtained by reacting the compound defined in 2) with the compound $NHR^2R^3$.

In the case where $R^1$ is to represent SH or $SR^2$, it is possible to react the compound defined in 2) with a halide $X^-$, which gives the compound with ($R^1$—X), which is then reacted with $HS^-$ or $R^2S^-$ to give a compound, where $R^1$ is to represent SH or $SR^2$.

When $R^1$ is to represent a hydrocarbon group, reaction takes place with $R_2^1LiCu$ ($R^1$ representing a hydrocarbon group) to give a final compound, where $R^1$ then represents a hydrocarbon group.

In the same way, the compound where $R^1$ represents a halogen can react with $CN^-$ to give a final compound, where $R^1$ will represent CN.

In addition, the compound where $R^1$ represents CN can, by controlled hydrolysis, give a compound where $R^1$ will represent $CONH_2$. The compound where $R^1$ represents CN can, by complete hydrolysis, give a compound where $R^1$ will represent COOH.

The compound where $R^1$ represents COOH can, by esterification, give a compound where $R^1$ will represent $COOR^2$.

The compound where $R^1$ represents COOH can react on $NHR^2R^3$ in the presence of DCC (dicyclohexylcarbodiimide) to give a compound where R1 will represent $NR^2R^3$.

The cyclodextrin derivatives according to the invention have numerous advantages. In particular, when they are persubsituted, i.e. when all the $R^1$ are different from the OH group, the derivatives have a good solubility in organic solvents, such as chloroform, acetone, tetrahydrofuran, etc. This solubility is of interest for their use in ionic separation, because it makes it possible to carry out the separation by liquid-liquid exchange processes, which are well known in the art.

Moreover, the possibility of introducing one or more particular chemical groups makes it possible to make to measure complexing agents for very varied ions. This is increased by the fact that the three natural cyclodextrins usable as a starting material, have different cavity diameters, which can lead to a supplementary selection relative to the size of the ions to be separated.

The starting products of formulas (III) or (IV) used in the invention can be prepared by conventional processes, such as those described in the aforementioned documents 1 and 2 of Gadelle A. et al. and Ashthon P. R. et al.

Other features and advantages of the invention can be better gathered from studying the following examples, given in an illustrative and non-limitative manner with reference to the attached drawing.

BRIEF DESCRIPTION OF THE DRAWING

FIGS. 1(a), 1(b) and 1(c) are nuclear magnetic resonance (NMR) spectra of the proton of the derivative of example 1 alone (a), or in the presence of 1 mmole/l of lead nitrate or in the presence of 3 mmole/l of lead nitrate.

DETAILED DESCRIPTION OF EMBODIMENTS

EXAMPLE 1

Preparation of Hexakis (3,6-Anhydro-2–0-methyl) cyclomaltohexaose

This compound complies with the above formula (I), in which all the $R^1$ represent $OCH_3$ and n is equal to 6.

Weighing takes place of 50 mg (0.057 mmole) of hexakis (3,6-anhydro)cyclomaltohexaose, dried in vacuo at 120° C. for 48 hours and 10 ml of anhydrous dimethyl formamide (DMF) are added thereto and the solution is heated for 15 minutes at 70° C. until a dispersion is obtained. 82 mg of sodium hydride dispersed in oil are weighed in another flask and to the same are added 10 ml of anhydrous DMF. Accompanied by stirring, to the latter flask and using a syringe is added the hexakis (3,6-anhydro) cyclomaltohexaose suspension. After stirring for 25 minutes, 200 ul of methyl iodide $CH_3I$ (3 mmole) are added with the syringe. After stirring for 15 minutes, the solvent is evaporated and the residue dissolved in water. The solution is washed with chloroform in order to eliminate the oils and the aqueous part is lyophilized. The latter undergoes chromatography on a polyamine PBMN column manufactured by Y.M.C. using a gradient of 0 to 30% water in acetonitrile and characterized by nuclear magnetic resonance of the proton at 500 MHz, a temperature of 298 K and a concentration of 3 mmole/l in $D_2O$.

The results obtained are shown in FIG. 1(a).

EXAMPLE 2

Formation of the Lead Complex

To an aqueous solution of the permethyl derivative obtained in example 1 is added an aqueous lead nitrate solution in order to obtain an aqueous solution containing 3 mmole/l of permethyl derivative and 1 mmole/l of lead nitrate. The solution obtained is analyzed by nuclear magnetic resonance under the same conditions as in example 1 (500 MHz, $D_2O$, 298 K).

The results obtained are given in FIG. 1(b).

In this case, the exchange is sufficiently slow compared with the NMR observation time, to observe the two signals corresponding to the free cyclodextrin (FIG. 1(a)) and to the complex (FIG. 1(b)). The respective surfaces of the free and complexed parts represent 2 for 1, which signifies that all the lead present is complexed.

In FIG. 1(b), a clear separation between the free and complexed cyclodextrin is visible for proton $H_1$ only. The widening of the signals is characteristic of a slow exchange.

EXAMPLE 3

Formation of a Lead Complex

The same operating procedure as in example 2 is followed, but the aqueous solution incorporates 3 mmole/l of the permethyl derivative of example 1 and 3 mmole/l of lead nitrate.

The NMR spectrum of the proton is shown in FIG. 1(c).

Here again, only the signals of the complex are visible. A single widened signal is observed for H1. Such a behaviour can be observed for an extremely high affinity constant.

EXAMPLE 4

Formation of the Lead Complex

The same operating procedure as in example 3 is followed, but addition also takes place of sodium nitrate so as to obtain an aqueous solution incorporating 3 mmole/l of the permethyl derivative of example 1, 3 mmole/l of lead nitrate and 3 mmole/l of sodium nitrate.

The NMR spectrum of the complex obtained is identical to that shown in FIG. 1(c).

Thus, the NMR spectrum of the complex is not modified by the presence of 3 mM sodium nitrate. This result is of vital importance with a view to applications in the biological field, because it shows that the lead can be complexed, even in the presence of an excess of sodium ions.

The NMR results obtained in examples 2 to 4 show that the affinity constant of the permethyl derivative of example 1 for Pb is much higher than that obtained with the starting hexakis (3,6-anhydro)cyclomaltohexaose, the latter being approximately $10^5$ in the case of the permethyl derivative and approximately 2500 in the case of the starting per (anhydro)cyclodextrin.

Thus, said permethyl derivative is of great interest, particularly for lead decontamination in living beings.

Thus, it is neither toxic, nor hemolytic, whereas the corresponding unmethylated per(3,6-anhydro)cyclodextrin is hemolytic. Moreover, it can complex lead, even in the presence of high sodium contents.

LIST OF CITED DOCUMENTS

Document 1: Gadelle A. and Defaye J., Angew. Chem. Int. Ed. Engl. 1991, 30, pp 79—79.
Document 2: Ashton P. R., Ellwood P., Staton I. and Stoddart J. F., Angew. Chem. Int. Ed. Engl. 1991, 30, pp 80–81.
Document 3: Yamamura H. and Fujita K., Chem. Pharm. Bull., 1991, 39, pp 2505–2508.
Document 4: Yamamura H., Esuka T., Kawase Y., Kawai M., Butsugan Y. and Fujita K., J. Chem. Soc., Chem. Commun., 1993, pp 636–637.
Document 5: Yamamura H., Nagaoka H., Kawai M. and Butsugan Y., Tetrahedron Lett., 1995, 3b, pp 1093–1094.
Document 6: Ashton et al, J. Org. Chem. 1995, 60, pp 3898–3903.

What is claimed is:
1. Derivative of per(3,6-anhydro)cyclodextrin complying with one of the following formulas:

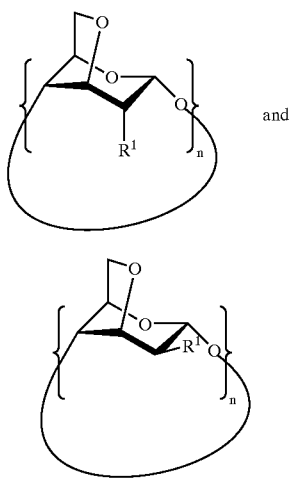

(I)

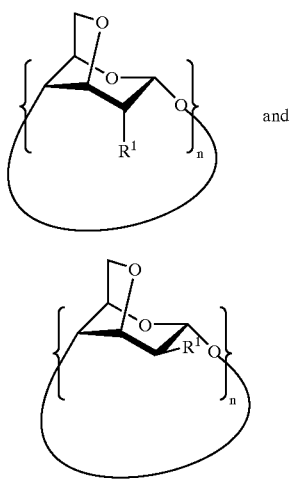

(II)

in which at least one of the $R^1$ represents the methoxy group and the other $R^1$, which can be the same or different, represent a group complying with one of the formulas: OH, $OR^2$, SH, $SR^2$, $OCOR^2$. $NH_2$, $NR^2R^3$, $CONR^2R^3$, $CONH_2$ CN, $COOR^2$, COOH and $R^2$, in which $R^2$ represents a saturated or unsaturated, aliphatic or aromatic hydrocarbon group, which can have one or more heteroatoms chosen from among O, S and N, and $R^3$ represents a hydrogen atom or a saturated or unsaturated, aliphatic or aromatic, hydrocarbon group, which can have one or more heteroatoms chosen from among O, S and N, and n is equal to 6, 7 or 8, provided that all the $R^1$ do not represent $OCH_3$ when n=7 and that the derivative complies with formula (I).

2. Derivative of per(3,6-anhydro)cyclodextrin according to claim 1 complying with formula (I), in which all the $R^1$ represents the $OCH_3$ group and n is equal to 6.

3. Complex of lead and a derivative of per(3,6-anhydro)cyclodextrin complying with one of the following formulas:

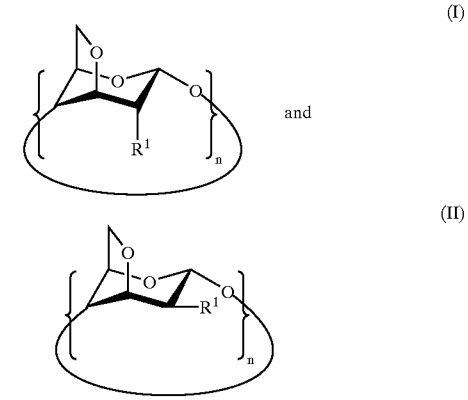

in which at least one of the $R^1$ represents the methoxy group and the other $R^1$, which can be the same or different, represent a group complying with one of the formulas: OH, $OR^2$, SH, $SR^2$, $OCOR^2$. $NH_2$, $NR^2R^3$, $CONR^2R^3$, $CONH_2$ CN, $COOR^2$, COOH and $R^2$, in which $R^2$ represents a saturated or unsaturated, aliphatic or aromatic hydrocarbon group, which can have one or more heteroatoms chosen from among O, S and N, and $R^3$ represents a hydrogen atom or a saturated or unsaturated, aliphatic or aromatic, hydrocarbon group, which can have one or more heteroatoms chosen from among O, S and N, and n is equal to 6, 7 or 8.

4. Complex according to claim 3, wherein n is equal to 6.

5. Complex according to claim 3, wherein the per(3,6-anhydro)cyclodextrin derivative complies with formula (I), in which all the $R^1$ represent the methoxy group and n is equal to 6.

6. Process for the fixation or separation of lead ions, which comprises contacting a medium containing said lead ions with a derivative of per(3,6-anhydro)cyclodextrin, complying with one of the following formulas:

(I)

(II)

in which at least one of the $R^1$ represents the methoxy group and the other $R^1$, which can be the same or different, represent a group complying with one of the formulas: OH, $OR^2$, SH, $SR^2$, $OCOR^2$. $NH_2$, $NR^2R^3$, $CONR^2R^3$, $CONH_2$ CN, $COOR^2$, COOH and $R^2$, in which $R^2$ represents a saturated or unsaturated, aliphatic or aromatic, hydrocarbon group, which can have one or more heteroatoms chosen from among O, S and N, and $R^3$ represents a hydrogen atom or a saturated or unsaturated, aromatic or aliphatic, hydrocarbon group, which can have one or more heteroatoms chosen from among O, S and N, and n is equal to 6, 7 or 8, for fixing said lead ions in complex form with the per(3,6-anhydro)cyclodextrin derivative and for separating them from said medium.

7. Process according to claim 6, wherein n is equal to 6.

8. Process according to claim 6, wherein the per(3,6-anhydro)cyclodextrin derivative complies with formula (I), in which all the $R^1$ represent the methoxy group and n is equal to 6.

9. Process according to claim 6 wherein said medium is an aqueous solution, the cyclodextrin derivative being dissolved in an organic solvent immiscible with the aqueous solution.

10. Process of lead decontamination of an animal which comprises the step of administering to an animal in need of lead decontamination a pharmaceutical composition comprises a per(3,6-anhydro)cyclodextrin derivative complying with one of the following formulas:

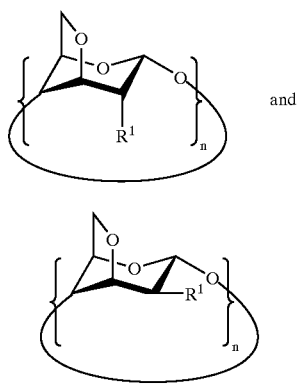

in which at least one of the $R^1$ represents the methoxy group and the other $R^1$, which can be the same or different, represent a group complying with one of the formulas: OH, $OR^2$, SH, $SR^2$, $OCOR^2$, $NH_2$, $NR^2R^3$, $CONR^2R^3$, $CONH_2$, CN, $COOR^2$, COOH and $R^2$, in which $R^2$ represents a saturated or unsaturated, aliphatic or aromatic, hydrocarbon group, which can have one or more heteroatoms chosen from among O, S and N, and $R^3$ represents a hydrogen atom or a saturated or unsaturated, aliphatic or aromatic, hydrocarbon group, which can have one or more heteroatoms chosen from among O, S and N, and n is equal to 6, 7 or 8.

11. The process of claim 10 wherein the per(3,6-anhydro) cyclodextrin derivative complies with formula (I), in which all the $R^1$ represent the methoxy group and n is equal to 6.

* * * * *